(12) United States Patent
Segura Martin et al.

(10) Patent No.: US 9,989,521 B2
(45) Date of Patent: Jun. 5, 2018

(54) METHOD FOR ISOLATING APOPTOTIC BODIES

(71) Applicants: Tomas Segura Martin, Albacete (ES); Oscar Ayo Martin, Albacete (ES); Gema Serrano De Las Heras, Albacete (ES)

(72) Inventors: Tomas Segura Martin, Albacete (ES); Oscar Ayo Martin, Albacete (ES); Gema Serrano De Las Heras, Albacete (ES)

(*) Notice: Subject to any disclaimer, the term of this patent is extended or adjusted under 35 U.S.C. 154(b) by 0 days. days.

(21) Appl. No.: 15/037,301

(22) PCT Filed: Nov. 14, 2014

(86) PCT No.: PCT/ES2014/070844
§ 371 (c)(1),
(2) Date: May 17, 2016

(87) PCT Pub. No.: WO2015/075288
PCT Pub. Date: May 28, 2015

(65) Prior Publication Data
US 2016/0290996 A1 Oct. 6, 2016

(30) Foreign Application Priority Data
Nov. 19, 2013 (ES) .................... 201331688

(51) Int. Cl.
*G01N 33/50* (2006.01)
(52) U.S. Cl.
CPC ..... *G01N 33/5091* (2013.01); *G01N 33/5005* (2013.01); *G01N 2333/705* (2013.01); *G01N 2510/00* (2013.01); *G01N 2800/28* (2013.01); *G01N 2800/285* (2013.01); *G01N 2800/2835* (2013.01); *G01N 2800/32* (2013.01); *G01N 2800/324* (2013.01); *G01N 2800/52* (2013.01); *G01N 2800/7028* (2013.01)
(58) Field of Classification Search
CPC ................ G01N 33/5091; G01N 2510/00
See application file for complete search history.

(56) References Cited

FOREIGN PATENT DOCUMENTS

| | | |
|---|---|---|
| WO | WO 2003/076589 A2 | 9/2003 |
| WO | WO 2011/154689 A1 | 12/2011 |
| WO | WO 2013/164289 A1 | 11/2013 |

OTHER PUBLICATIONS

Orozco et al. "Flow cytometric analysis of circulating microparticles in plasma". Cytometry A. Jun. 2010; 77(6): 502-514. doi:10.1002/cyto.a.20886, pp. 1-25.*
Witwer et al. "Standardization of sample collection, isolation and analysis methods in extracellular vesicle research". Journal of Extracellular Vesicles. 2013, 2: 20360—http://dx.doi.org/10.3402/jev.v2i0.20360, pp. 1-25; published May 27, 2013.*
Crescitell et al., "Distinct RNA profiles in subpopulations of extracellular vesicles: apoptotic bodies, microvesicles and exosomes," *Journal of Extracellular Vesicles* 2: 20677 (10 pages) (Sep. 12, 2013).
Elliott et al., "Apoptosis induces neuronal apolipoprotein-E synthesis and localization in apoptotic bodies," *Neuroscience Letters* 416: 206-210 (2007).
Holtom et al., "Microparticle formation after co-culture of human whole blood and umbilical artery in a novel in vitro model of flow," *Cytometry Part A: The Journal of the International Society for Analytical Cytology* 81(5): 390-399 (published online Dec. 29, 2011).

* cited by examiner

*Primary Examiner* — Vera Afremova
(74) *Attorney, Agent, or Firm* — Klarquist Sparkman, LLP

(57) ABSTRACT

The invention pertains to the field of the study of apoptosis, especially the field of the prognosis and monitoring of diseases wherein apoptosis occurs. Concretely, the invention relates to a method for isolating apoptotic bodies from a sample of body fluid, and to methods for the prognosis and evaluation of the efficiency of a treatment for vascular, neurodegenerative and/or oncological diseases, based on the use of said method for isolating apoptotic bodies.

8 Claims, 7 Drawing Sheets

METHOD FOR ISOLATING APOPTOTIC BODIES

CROSS REFERENCE TO RELATED APPLICATIONS

This is a § 371 U.S. national stage of International Application No. PCT/ES2014/070844, filed Nov. 14, 2014, which was published in Spanish, which claims priority to Spanish Patent Application No. P201331688, filed Nov. 19, 2013.

TECHNICAL FIELD

The present invention belongs to the field of apoptosis. Specifically, it relates to a method for the isolation of apoptotic bodies from body fluids and the use of said method and isolated apoptotic bodies for the evaluation of apoptotic processes, particularly in pathologies such as vascular, neurodegenerative and oncological diseases.

BACKGROUND OF THE INVENTION

Apoptosis is a kind of ordered cell death, which depends on the implementation of a cascade of molecular events that culminate in the total disintegration of the cell. In the late stage of apoptosis, and as a result of cell fragmentation, small membranous vesicles called apoptotic bodies are generated.

Under physiological conditions, apoptosis is involved in morphogenesis and in tissue remodeling during the development, and the regulation of the immune system and homeostasis. However, this process also plays a key role in the cell and tissue death that occurs in various pathologies, such as vascular diseases, neurodegenerative diseases and oncological diseases. The evaluation of the apoptotic processes, namely assessing the degree of apoptosis or apoptotic index in these diseases would be useful in daily clinical practice, since it would allow an earlier and more accurate prognosis, more effective monitoring of the evolution of the disease, and the selection of the most appropriate treatment for each patient.

However, the in vivo analysis of apoptosis that occurs in tissue has a clear limitation as it is currently necessary to obtain tissue samples of patients by interventionist methods, biopsy or surgery. Therefore, there is an urgent medical need for non-invasive procedures that allow the study of apoptosis, preferably in a quick, simple and quantitative manner.

In the state of the art, a large number of studies that focus on determining the death of a tissue, particularly through the collection and analysis of solid samples taken by non-invasive methods such as biopsies (tissue samples) can be found. The degree of apoptosis is determined by various techniques known by the person skilled in the art, such as detection of DNA fragmentation (TUNEL technique, for example) and detecting the phosphatidylserine present on the outside of the plasma membrane of apoptotic cells with Annexin V. However, in these methods the patients' samples are obtained by invasive methods. Moreover, in most cases primary cultures of the biopsies are taken and subsequently apoptosis is induced in order to isolate apoptotic bodies (WO 99/58645 A1), that is, the apoptotic bodies are isolated in non-physiological conditions (artificial induction of apoptosis).

Surprisingly, the authors of the present invention have developed a method for isolating apoptotic bodies through centrifugation of samples of body fluids. That is, these apoptotic bodies are isolated in physiological conditions, without previous artificial induction of apoptosis. Moreover, with this method up to more than 90% of all apoptotic bodies from the sample of body fluid can be isolated and, besides, the apoptotic bodies maintain their integrity and are therefore detectable and measurable. In this sense, WO 03/076589 A2 describes methods for detecting and analysing apoptotic bodies from body fluids. Among the various methods described, there is one in which apoptotic bodies from the cell fraction are separated by centrifugation. In a preferred embodiment, the biological sample is blood and it is centrifuged at more than 500 g, preferably between 800 g and 1,200 g, so that the apoptotic bodies remain in the plasma fraction. If it is desirable to separate or isolate these apoptotic bodies from the plasma, another high speed centrifugation is performed (speed not defined, for the person skilled in the art of the present invention, a high speed corresponds to a speed higher than 60,000 g), after which the apoptotic bodies remain in the sediment. However, unlike what is achieved with the method of the present invention, with the conditions described in WO 03/076589 it is not possible to isolate up to 90% of all the apoptotic bodies present in the body fluids, nor maintain their integrity. First, this is due to the fact that a centrifugation speed higher than 500 g, aimed at obtaining plasma or serum, leads to the sedimentation of all cellular blood components, among which are platelets. These cells easily form aggregates, especially in the presence of other kind of blood cells such as erythrocytes and leukocytes. If this occurs, the apoptotic bodies would be retained in the cell aggregates and centrifugation at a speed higher than 500 g would lead to their sedimentation with the cell fraction, and this would mean losing a large number of them. Furthermore, the high speed centrifugation of plasma or serum obtained from the first centrifugation could result in rupture of the apoptotic bodies and in their contamination with other smaller membrane vesicles. Due to these drawbacks, the apoptotic bodies isolated by the method described in WO 03/076589 A2 have little or no utility for prognosis and/or monitoring of the treatment for subjects with diseases associated with apoptosis, as the number of isolated apoptotic bodies would be much lower than the real number in the body fluid and the apoptotic bodies could be disintegrated and/or contaminated by other microvesicles, resulting in an erroneous quantification of apoptotic bodies.

Surprisingly, the authors of the present invention have developed a method for isolating apoptotic bodies that maintain their integrity and can therefore be quantified. Furthermore, the method of the invention minimizes to the maximum the loss of apoptotic bodies during isolation and achieves the isolation of more than 90% of all apoptotic bodies present in the body fluid sample. In this way, the authors of the present invention have developed a very useful tool for the study of apoptosis. Thus, the present invention also relates to a prognosis method based on the quantification of isolated apoptotic bodies by the method of the invention and to the use of such apoptotic bodies as a prognostic factor and as a marker of the efficacy of a therapeutic treatment. Finally, another important advantage of the integrity of apoptotic bodies isolated by the method of the present invention is its use in order to identify the cell type of the cell that has died from apoptosis, which provides information exceptionally useful in the clinical field, in particular in neurodegenerative, vascular and oncological diseases.

OBJECT OF THE INVENTION

The present invention relates, in a first aspect, to a method for the isolation of apoptotic bodies (method of the invention) which comprises the following steps:
  a) centrifuging a sample of body fluid taken from a subject, at a speed of 300 g or less, and collecting the supernatant,
  b) centrifuging the supernatant obtained in step a) at a speed between 400 g and 1000 g and collecting the supernatant,
  c) centrifuging the supernatant obtained in step b) at a speed between 8,000 g and 40,000 g and eliminating the supernatant,
wherein the sediment obtained in step c) comprises the isolated apoptotic bodies.

A second aspect of the present invention relates to a method of prognosis of a vascular disease comprising the following steps:
  i) isolating apoptotic bodies of a first and a second body fluid sample taken from a patient with a vascular disease by the method of the invention, wherein the second sample is taken at least 48 h after the first sample,
  ii) quantifying apoptotic bodies isolated in step i), and
  iii) comparing the number of apoptotic bodies isolated in the two samples, wherein a higher number of apoptotic bodies in the second sample compared with the first sample is indicative of a poor prognosis.

A third aspect of the present invention relates to a method for determining the stage of a neurodegenerative disease comprising the following steps:
  I) isolating apoptotic bodies in a body fluid sample taken from a patient with a neurodegenerative disease by the method of the invention,
  II) quantifying apoptotic bodies isolated in step I), and
  III) comparing the number of apoptotic bodies isolated from the sample with reference values.

A fourth aspect of the present invention relates to a method for analysing the effectiveness of a treatment of a vascular disease characterised in that it comprises the following steps:
  A) isolating apoptotic bodies of two samples of body fluid taken from a patient with a vascular disease by the method of the invention, wherein a first sample is taken before treatment and a second sample is taken after treatment, or where the two samples are taken during treatment, a first sample after treatment begins and a second sample at least 48 hours after the first,
  B) quantifying apoptotic bodies isolated in step A), and
  C) comparing the number of apoptotic bodies isolated in the two samples, wherein a lower number of apoptotic bodies in the second sample than in the first one indicates that the treatment is effective.

A fifth aspect of the present invention relates to a method for analysing the effectiveness of a treatment of an oncological and/or neurodegenerative disease characterised in that it comprises the following steps:
  A) isolating apoptotic bodies of two samples of body fluid taken from a patient with an oncological and/or neurodegenerative disease by the method of the invention, wherein a first sample is taken before treatment and a second sample is taken after treatment, or where the two samples are taken during the treatment, a first sample once the treatment has begun and a second sample at least two weeks after taking the first one,
  B) quantifying apoptotic bodies isolated in step A), and
  C) comparing the number of apoptotic bodies in the two samples, wherein in the oncological disease a number of apoptotic bodies in the second sample higher than in the first one indicates that the treatment is effective and in the neurodegenerative disease a number of apoptotic bodies in the second sample lower than in the first one indicates that the treatment is effective.

A sixth aspect of the present invention relates to a method for identifying the cell type of a cell dead from apoptosis, which comprises the following steps:
  1) isolating apoptotic bodies from a body fluid sample by the method of the invention,
  2) detecting a cell type marker in the outside of the plasma membrane of an apoptotic body.

A seventh aspect of the present invention relates to the use of the method of the invention for prognosis of a vascular and/or neurodegenerative disease.

An eighth aspect of the present invention relates to the use of the method of the invention for evaluating the effectiveness of the treatment of an oncological, neurodegenerative and/or vascular disease.

A ninth aspect of the present invention relates to the use of the method of the invention for identifying the cell type of a cell dead from apoptosis.

DETAILED DESCRIPTION OF THE INVENTION

Figure 1:
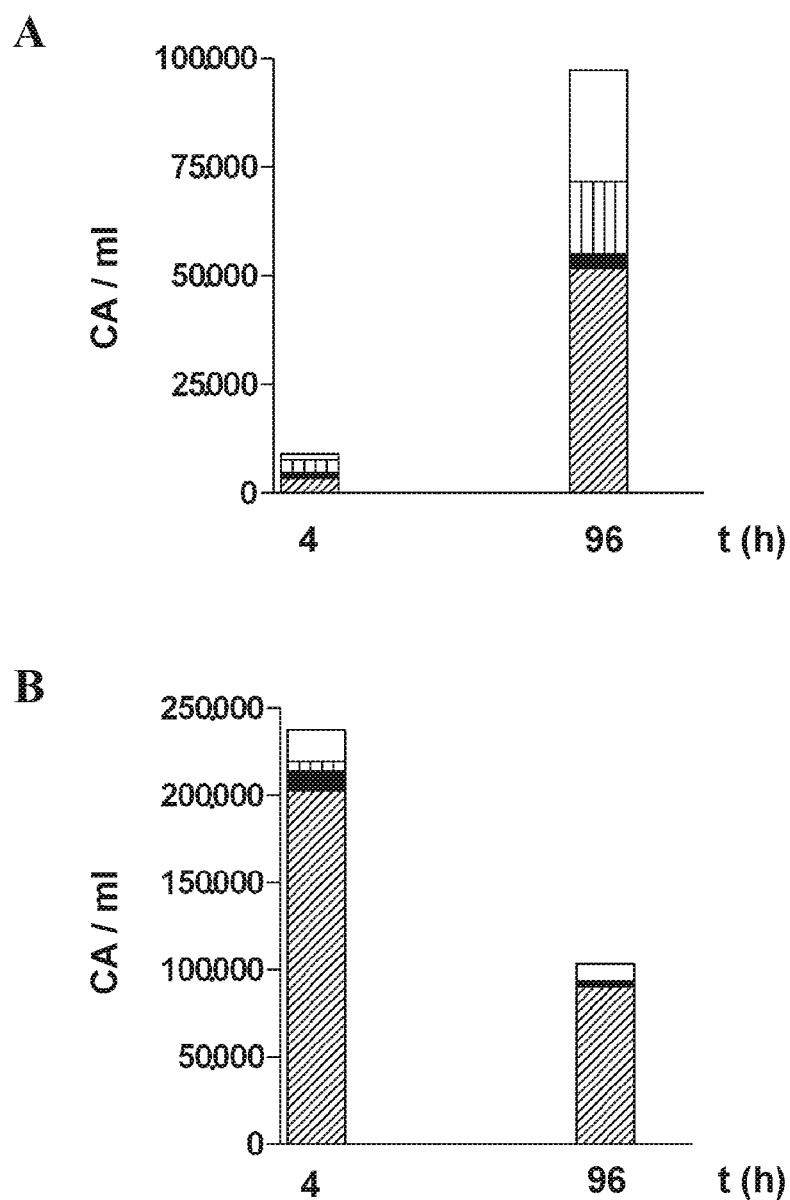
FIG. 1: Graphic representation of the number of apoptotic bodies (also called AB hereinafter) per milliliter of plasma in patients suspected of ischemic stroke, versus time in hours. In particular, the data are shown at 4 and 96 h post-stroke. The AB from the cell death of various cell types are represented: microglia (white), oligodendrocytes (vertical stripes), neurons (black) and astrocytes (oblique lines). Panel A: patient with cerebral infarction of undetermined origin. Panel B: patient with cerebral infarction of cardioembolic origin.

The present invention relates in a first aspect to a method for isolating apoptotic bodies which comprises the following steps:
a) centrifuging a sample of body fluid taken from a subject, at a speed of 300 g or less, and collecting the supernatant,
b) centrifuging the supernatant obtained in step a) at a speed between 400 g and 1000 g and collecting the supernatant,
c) centrifuging the supernatant obtained in step b) at a speed between 8,000 g and 40,000 g and eliminating the supernatant,
wherein the sediment obtained in step c) comprises the isolated apoptotic bodies.

The temperature and time conditions in which the centrifugations of the method of the present invention are held are easily determinable by the person skilled in the art. In a particular embodiment, they are carried out at a temperature between 8° C. and 41° C., more particularly between 12° C. and 25° C., and for at least 5 minutes. The method of the present invention is preferably performed during the next three hours after collecting the body fluid sample. Preferably, the sample is maintained under gentle shaking until the beginning of the isolation method.

In the present invention the term "apoptotic body" refers to a membrane vesicle, of a size from 1 µm to 4 µm, which is caused by the death of cells from apoptosis, and which contains nuclear fragments, genetic material and cytoplasmic constituents of the apoptotic cell. The term "body fluid" refers to extracellular body liquid.

In a particular embodiment of the method of the present invention, the body fluid is selected from the group consisting of blood, plasma, urine, cerebrospinal fluid, ascetic fluid, synovial fluid and amniotic fluid. In another particular embodiment, the aforementioned body fluid is blood, plasma or urine. In a further particular embodiment, the aforementioned body fluid is blood or plasma, and in a preferred embodiment the body fluid is blood.

The use of serum samples to remove circulating apoptotic bodies, in the present invention, is not recommended, since blood serum is the component of the resultant blood after allowing its clotting and excluding the fibrin clot and other components, and during the formation of the clot, apoptotic bodies may be retained in the fibrin network and its elimination would imply the loss of a large number of apoptotic bodies. Thus, in a particular embodiment, when the body fluid sample is blood, the sample is collected in an anticoagulant medium. In a particular embodiment, the anticoagulant is selected from the group consisting of sodium citrate, sodium EDTA, potassium EDTA, sodium heparin, potassium heparin, lithium heparin, ammonium heparin, sodium fluoride and mixtures thereof. In a preferred embodiment the anticoagulant is sodium citrate.

In step a) of the method of the invention the speed of centrifugation cannot be higher than 300 g, since that would result in the sedimentation of all the cellular components of blood, including platelets, which would drag with them a large proportion of the apoptotic bodies in the sample, leading to the loss of a large number of apoptotic bodies. In a particular embodiment of the invention, the speed of centrifugation in step a) is between 160 g and 300 g. This speed range makes it possible to achieve the minimal loss of apoptotic bodies with the sediment.

Step b) of the method of the invention is necessary to obtain a supernatant rich in apoptotic bodies and free of platelets and those cellular components that have not settled with the centrifugation of step a). However, a speed higher than 1,000 g might result in the loss of apoptotic bodies which settle with the platelets and those cellular components which have not settled by centrifugation of step a). The preferred condition to isolate the largest number of apoptotic bodies as possible from the supernatant obtained in step a) is a centrifugation at a speed between 500 g and 800 g. Thus, in a particular embodiment of the invention, step b) is performed at a speed of between 500 g and 800 g.

The supernatant obtained in step b) comprises in addition to apoptotic bodies, other circulating microvesicles such as microparticles and exosomes. Circulating microparticles are membranous vesicles secreted by activation of different cell types, most notably; endothelial cells, epithelial cells, leukocytes and platelets. These microparticles have a size of 0.1 µm-1 µm and are constituted by the evagination of the plasma membrane, while exosomes have a smaller size (0.05 µm-0.1 µm) and proceed from an intracellular compartment: the multivesicular bodies (MVB).

The purpose of step c) of the method of the invention is to settle the apoptotic bodies with the minimum concentration of other circulating microvesicles. A centrifugation speed lower than 8,000 g would not achieve the sedimentation of all apoptotic bodies present in the supernatant obtained from step b) and a speed exceeding 40,000 g would provoke the rupture of the apoptotic bodies and the sedimentation of other circulating microvesicles. In a particular embodiment of the invention, the speed of the centrifugation in step c) is between 11,000 g and 30,000 g, with which the sedimentation of other kinds of microvesicles decreases notably. By removing the supernatant, it remains sediment which comprises the isolated apoptotic bodies. These apoptotic bodies may be resuspended and stored at a temperature between 4° C. and 8° C. The bodies may be resuspended in TBS (Tris-buffered saline, 2 mM Tris, 150 mM NaCl, pH:7.4), PBS (Phosphate-buffered saline, 10 mM phosphate, 137 mM NaCl, 2.7 mM KCl pH:7.4), Hepes (4-(2-hydroxyethyl)-1-piperazineethanesulfonic acid) 10-50 mM CHES (N-Cyclohexyl-2-aminoethanesulfonic acid) 10-50 mm, MOPS (3-N-morpholino)propanesulfonic acid) 10-50 mM and PIPES (piperazine-N,N'-bis(2-ethanesulfonic acid) 10-50 mM. The resuspended apoptotic bodies can be stored for up to twelve months, preferably up to six months. Apoptotic bodies resuspended in buffer referred to hereinafter as preparation of apoptotic bodies.

An important advantage of the method of the present invention is that in the sediment comprising isolated apoptotic bodies the proportion of other microparticles is lower than 20% (Table 1, Example 1). This degree of purity of apoptotic bodies in the sediment obtained in step c) of the method of the invention has a great clinical significance, as will be explained later.

Moreover, another important advantage of the method of the present invention is its high performance in the isolation of apoptotic bodies. With the method of the present invention it is possible to isolate at least 75% of the apoptotic bodies present in the body fluid sample (Table 2, Example 2). Surprisingly, it can even isolate a higher percentage of apoptotic bodies by diluting the supernatant obtained in step a) in a buffer or pH buffer solution before carrying out step b). Thus, in a particular embodiment of the method of the invention, between steps a) and b) is carried out step a1) in which the supernatant obtained in step a) is diluted in a buffer. With this particular embodiment, the number of isolated apoptotic bodies can increase to a percentage of 80% or more of apoptotic bodies present in the sample of body fluid and even to a percentage of 90% or more (Table 2, Example 2).

Buffers compatible with body fluids are known by the person skilled in the art. In a particular embodiment, the buffer of step a1 is selected from the group consisting of TBS, PBS, HEPES 10-50 mM, CHES 10-50 mM, MOPS 10-50 mM and PIPES 10-50 mM. In a preferred embodiment, the buffer is TBS. In another preferred embodiment, the dilution is 1:3 supernatant:buffer.

Unexpectedly, with the method of the present invention it is possible to obtain intact apoptotic bodies. In the context of the present invention "intact apoptotic bodies" refers to apoptotic bodies with an intact plasma membrane, without ruptures, this means that the apoptotic bodies are not broken or disintegrated. This allows the quantification of the aforementioned apoptotic bodies, not only the analysis or detection of their components when they get broken as typically occurs in the isolation methods of apoptotic bodies described in the state of the art. The quantification of the apoptotic bodies is clinically very useful as a method of prognosis and as a method for evaluating the effectiveness of a therapeutic treatment. Such clinical usefulness is enhanced by the high purity degree of the isolated bodies by the method of the present invention, with which, as noted above, a sediment is obtained wherein over 80% are apoptotic bodies. The presence of other microvesicles in that sediment would hinder its clinical utility as it would result in an incorrect quantification of apoptotic bodies. The detection and quantification of apoptotic bodies is based on the specific binding of annexin V to a lipid, phosphatidylserine, present on the outside of their plasma membrane. It has been described that the microparticles also contain the mentioned lipid, therefore, they would be quantified as if they were apoptotic bodies and the number of quantified apoptotic bodies would therefore be higher than the number of physiological ones.

All these advantages make the method of the present invention an extremely valuable tool in clinical practice as a non-invasive method to determine the degree of cell death that has occurred in a subject, which would allow an earlier and more accurate prognosis, a more effective monitoring, and the selection of the most appropriate treatments, and therefore a personalized therapy in various diseases, including neurodegenerative, vascular and oncological diseases. In the context of the present invention, the term "non-invasive method" refers to a method in which injections (for removal of body fluids) are performed or tools superficially in contact with the patient or at some distance are used. Unlike invasive methods, in these non-invasive techniques it is not necessary to make an incision to reach the site or tissue of interest.

In this way, a second aspect of the present invention relates to a method of prognosis of a vascular disease characterised in that it comprises the following steps:
  i) isolating apoptotic bodies of a first and a second body fluid sample taken from a patient with a vascular disease by the method of the invention following the first aspect of the invention, wherein the second sample is taken at least 48 h after taking the first sample,
  ii) quantifying apoptotic bodies isolated in step i), and
  iii) comparing the number of apoptotic bodies isolated in the two samples, wherein a higher number of apoptotic bodies in the second sample compared with the first sample is indicative of a poor prognosis.

In the context of the present invention, the term "poor prognosis", also referred to as unfavourable prognosis in the state of the art relates to a low chance of recovery, and thus to an increased risk or likelihood of death. The term "vascular disease" relates to all types of pathology or disease induced or caused by the injury or compression of a blood vessel. In a particular embodiment of the invention, the vascular disease is selected from the group consisting of cardiovascular and cerebrovascular diseases and thrombosis. In a more particular embodiment of the invention, the vascular disease is a cerebrovascular disease. In another particular embodiment, the first and second samples are taken at least 72 h apart, and more particularly, at least 92 h apart. In a preferred embodiment, the samples are taken 92 h apart.

Figure 2:
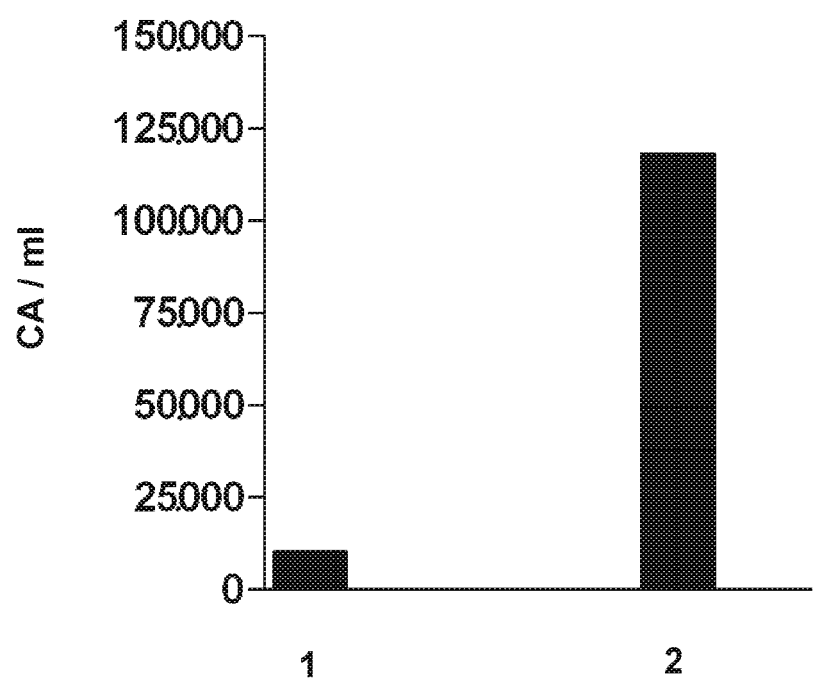
FIG. 2: Graphic representation of the number of AB per milliliter of plasma in two patients suspected of ischemic stroke. The analysis determined that the patient 1 (1 in x-axis) suffered a transient ischemic attack (TIA) and patient 2 (2 in x-axis) suffered an ischemic stroke. The AB were isolated without dilution.
Figure 3:
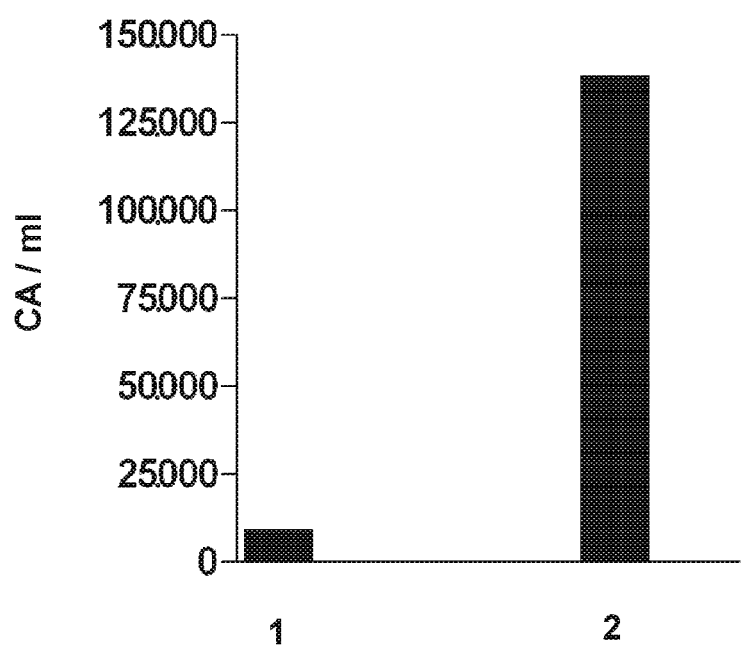
FIG. 3: Graphic representation of the number of AB per milliliter of plasma in two patients suspected of ischemic stroke. The analysis determined that the patient 1 (1) suffered a TIA and patient 2 (2) suffered an ischemic stroke.

Thus, the use of the isolation method of AB in the present invention according to the first aspect of the invention makes it possible to predict the prognosis of a subject affected by a vascular disease based on the quantification of apoptotic bodies, quickly and easily and from a body fluid sample (see Examples 3, 4 and 5, FIGS. 1, 2 and 3 respectively).

The quantification of the apoptotic bodies isolated by the method according to the first aspect of the invention also serves to determine the stage of a neurodegenerative disease. Thus, a third aspect of the present invention relates to a method for determining the stage of a neurodegenerative disease characterised in that it comprises the following steps:
  I) isolating apoptotic bodies in a body fluid sample taken from a patient with a neurodegenerative disease by the method of the invention,
  II) quantifying apoptotic bodies isolated in step I), and
  III) comparing the number of apoptotic bodies isolated from the sample with reference values.

In the context of the present invention, the term "neurodegenerative disease" relates to a group of chronic diseases of the nervous system, characterised by progressive neuronal (grey matter) and/or glial (white matter) loss. Several genetic and environmental factors are involved in the aetiology of the neurodegenerative diseases, causing disorders in the cognitive, sensory and motor systems. In a particular embodiment of the invention, the neurodegenerative disease is selected from the group consisting of multiple sclerosis, amyotrophic lateral sclerosis (ALS), Alzheimer's, Parkinson's and Huntington's disease. In a more particular embodiment of the invention, the neurodegenerative disease is selected from the group consisting of multiple sclerosis, Alzheimer's and Parkinson's disease.

With this method, it is possible to identify the stage of a neurodegenerative disease and therefore the prognosis of the said disease. In the case of neurodegenerative diseases, the levels of apoptotic bodies in a body fluid sample in early stages are higher than in advanced stages. Particularly, in the case of the neurodegenerative diseases in early stages, the levels of apoptotic bodies are higher than 30,000 AB per ml of plasma, and in advanced stages they are lower than 30,000 AB per ml of plasma. Thus, in a particular embodiment of the method of the invention, a number of AB per ml of plasma higher than 30,000, in particular 30,000 to 150,000, indicates that the neurodegenerative disease is in early stages, and a number of AB per ml of plasma lower than 30,000, particularly 5,000 to 20,000, indicates that the neurodegenerative disease is in an advanced stage. For example, a subject with Parkinson's disease and with a number of AB per ml of plasma higher than 30,000 would be in stage I or II, and with multiple sclerosis and a number of AB per ml of plasma lower than 30,000 would be in an advanced stage of the disease (see Examples 7 and 8, FIGS. 5 and 6 respectively).

The present invention also relates to a method for analysing the effectiveness of the treatment received by a subject with an oncological, neurodegenerative and/or vascular disease.

Thus, a fourth aspect of the present invention relates to a method for analysing the effectiveness of a treatment of a vascular disease characterised in that it comprises the following steps:
A) isolating apoptotic bodies from two body fluid samples taken from a patient with a vascular disease by the method of the invention following the first aspect of the invention, wherein a first sample is taken before treatment and a second sample is taken after treatment, or where the two samples are taken during the treatment, a first sample after the treatment has begun and a second sample at least 48 hours after taking the first one,
B) quantifying apoptotic bodies isolated in step A), and
C) comparing the number of apoptotic bodies isolated in the two samples, wherein a lower number of apoptotic bodies in the second sample compared with the first sample indicates that the treatment is efficient.

In a more particular embodiment of this method, the samples of step A) are taken at least 72 h apart, and more particularly, at least 92 hours apart and preferably 92 h apart.

A fifth aspect of the present invention relates to a method for analysing the effectiveness of a treatment of an oncological and/or neurodegenerative disease characterised by comprising the following steps:
A) isolating apoptotic bodies of two body fluid samples taken from a patient with an oncological and/or neurodegenerative disease by the method of the invention following the first aspect of the invention, wherein a first sample is taken before treatment and a second sample is taken after treatment, or where the two samples are taken during the treatment, a first sample after the treatment has begun and a second sample at least two weeks after taking the first one,
B) quantifying apoptotic bodies isolated in step A), and
C) comparing the number of apoptotic bodies in the two samples, wherein in the oncological disease a larger number of apoptotic bodies in the second sample than in the first indicates that the treatment is effective and in the neurodegenerative disease a lower number of apoptotic bodies in the second sample than in the first indicates that the treatment is effective.

In the case of the oncological diseases, anti-tumour treatments: chemotherapy, radiation and biological therapies are aimed at killing tumour cells by inducing apoptosis and therefore its disintegration. If the patient responds to the treatment, that means, the therapy works, is effective, tumour death occurs, and therefore higher levels of apoptotic bodies are detected in the second body fluid sample than in the first (see Example 9 FIG. 7).

Figure 4:
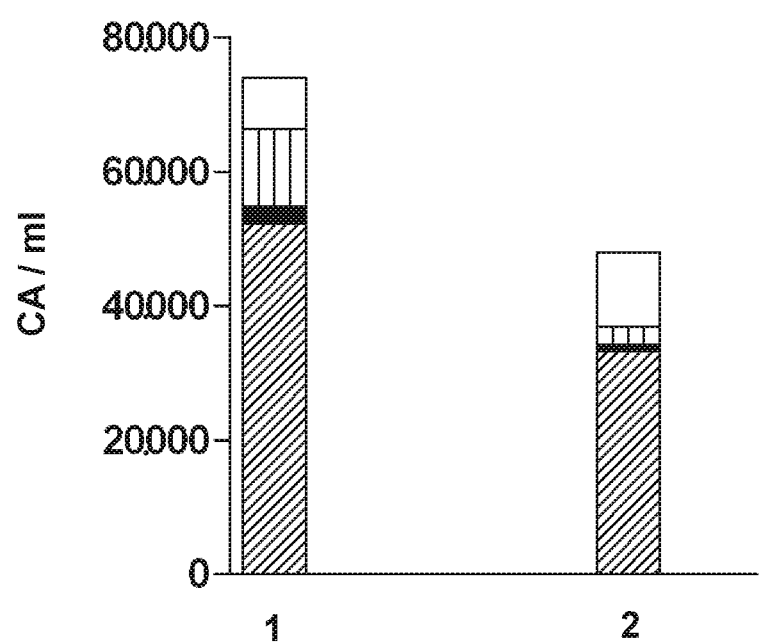
FIG. 4: Graphic representation of the number of AB per milliliter of plasma in two patients diagnosed with relapsing-remitting multiple sclerosis. Patient 1 (1) receives treatment with interferon beta and patient 2 (2) with natalizumab. The apoptotic bodies proceeding from the cell death of various cell types are represented: microglia (white), oligodendrocytes (vertical stripes), neurons (black) and astrocytes (oblique lines).

In the case of a neurodegenerative and/or vascular disease, if the patient responds to the treatment (therapy is effective), lower levels of apoptotic bodies are detected in the second body fluid sample than in the first (see Example 6, FIG. 4, for a neurodegenerative disease).

In the context of the present invention, oncological diseases relate to a group of diseases that are caused by tumour development. The tumour often invades the surrounding tissues and may metastasize to distant sites of the organism.

In a particular embodiment, the oncological disease is selected from the group consisting of colorectal cancer, pancreas, stomach, oesophagus, liver, lung, breast, ovarian, uterine, prostate, testicular, thyroid, head and neck, brain tumours (gliomas and neuroblastomas) and melanomas. In a more particular embodiment, the oncological disease is selected from the group consisting of colorectal cancer and liver cancer.

The integrity of the apoptotic bodies isolated by the method according to the first aspect of the present invention makes it possible to identify, in addition to its quantification, the cell type from which they derive, that is, it enables the identification of the cell type dead from apoptosis. This information is clinically very important in vascular, neurodegenerative and oncological diseases, and especially in the field of neurodegenerative and cerebrovascular diseases. Depending on the type of cell in the nervous system which is dead, the severity of the disease will be higher or lower and will influence its evolution or prognosis. For example, two patients with an ischemic stroke in which an increase of the apoptotic bodies is detected on the second body fluid sample (at least 48 hours after taking the first sample) have a poor prognosis. In addition, the disease can worsen, or in other words, the prognosis may worsen if the number of neurons proceeding from apoptotic bodies is very high, since they have little capacity for regeneration compared with the other cells of the nervous system, such as astrocytes, for example. Another example, two patients with multiple sclerosis, with the same number of apoptotic bodies in the body fluid sample, the subject whose number of apoptotic bodies proceeding from oligodendrocytes is higher will have a poorer prognosis. Oligodendrocytes are the cellular components responsible of the neuronal myelination of the neuronal axons, a higher process of demyelination goes along with a worsening of the disease. Furthermore, the identification of cell type that has died from apoptosis is clinically very relevant in oncological diseases, especially in the evaluation of the effectiveness of an anti-tumour treatment. For example, two patients diagnosed with colon cancer who received chemotherapy treatment where high plasma levels of apoptotic bodies after therapy are detected are indicative of effectiveness of the said treatment. In this context, a higher number of apoptotic bodies (AB per ml of sample) proceeding from tumour cells indicate higher effectiveness of such treatment.

Thus, a sixth aspect of the present invention relates to a method for identifying the cell type of a cell dead from apoptosis, characterised in that it comprises the following steps:
1) isolating apoptotic bodies from a body fluid sample by the method of the invention,
2) detecting a cell type marker in the outside of the plasma membrane of an apoptotic body.

In the context of the present invention, the term "cell type marker" relates to a protein that is specific or appears only in one cell type. Specifically, in the present invention the mentioned protein must be on the outside of the plasma membrane of the cell or be a transmembrane protein. In this method, one or more cell type markers may be detected.

In a particular embodiment of the method for identifying the cell type of a cell that has died from apoptosis, the cell type marker is a neuronal marker, and more particularly, the said neuronal marker is selected from the group consisting of CD90 (neuronal cell adhesion molecule L1), NGFR (nerve growth factor receptor) p75, PSA-NCAM, Ephrin-A2, Ephrin-A4, Ephrin-A5, Ephrin-B1, Ephrin-B2, GAP-43, Laminin-1, NAP-22, Netrin-1, Neurophilin, Plexin-A1, Semaphorin 3A, Semaphorin 3F, Semaphorin 4D, Trk A, Enkephalin, GAD65 (glutamate decarboxylase), GAP-43 (growth associated protein 43), LINGO-1 subunit of Na+/K+ ATPase, choline transporter, dopamine transporter (DAT), norepinephrine transporter (NET), serotonin transporter (SERT), transporter 1, 2 and 3 of GABA, neuronal glutamate transporter, AMPA receptor-binding protein (ABP), Complexine 1 (CPLX1), Contactin-1, VAMP-2, vesicular acetylcholine transporter (VAChT), vesicular GABA transporter (VGAT; VIAAT), vesicular glutamate transporter 1, 2, 3 (VGLUT), vesicular monoamine transporter 1, 2 (VMAT) and N-cadherin, E-cadherin.

In a particular embodiment of the method to identify the cell type of a cell that has died from apoptosis, the cell type marker is a glial marker, and more particularly, that glial marker is selected from the group consisting of GLAST, CD11b, CD100, CD104 and NG2 chondroitin sulphate proteoglycan. In a more particular embodiment of the method for identifying the cell type of a cell that has died from apoptosis, the cell type marker is selected from the group consisting of CD90, GLAST, CD11b, and CD100. In this way are identified neurons, astrocytes, microglia and oligodendrocytes, respectively (see Examples 3 and 6, FIGS. 1 and 4 respectively).

As for oncological diseases, any tumour antigen described in the state of the art serves as a cell type marker. In a particular embodiment of the method for identifying the cell type of a cell that has died from apoptosis, the cell type marker is a tumour antigen selected from the group consisting of carcinoembryonic antigen (CEA), prostate-specific membrane antigen (PSMA), mucins, integrins and receptors tyrosine kinases. Mucins include CA-125, CA-19-9 and AC-15-3, integrins include EpCAM (epithelial cell adhesion molecule), CD24, CD44, CD49, CD100 and CD104 and receptors tyrosine kinases include EGFR (epidermal growth factor receptor), FGFR (fibroblast growth factor receptor), VEGFR (vascular endothelial growth factor receptor), PDGF (platelet-derived growth factor receptor), and the insulin receptor.

Thus, in another particular embodiment of the method for identifying the cell type of a cell that has died from apoptosis, the cell type marker is selected from the group consisting of CD90, GLAST, CD11b, CD100 and tumour antigens.

The quantification of AB that is conducted in any of the methods described in the second, third, fourth, fifth and sixth aspect of the present invention can be accomplished by means of conventional techniques well known to the person skilled in the art. In a particular embodiment, the quantification of AB is performed by means of a method selected from the group consisting of flow cytometry, NanoSight® NTA "nanoparticle tracking analysis" technology, and impedance technology. In a preferred embodiment, the quantification of AB is performed by means of flow cytometry or NanoSight® NTA technology.

A seventh aspect of the present invention relates to the use of the method of the invention following the first aspect of the invention for the prognosis. A particular embodiment of this aspect relates to the use of the method of the invention for prognosticating vascular and/or neurodegenerative diseases.

An eighth aspect of the present invention relates to the use of the method of the invention for evaluating the effectiveness of the treatment for an oncological, neurodegenerative and/or vascular disease.

A ninth aspect of the present invention relates to the use of the method of the invention for identifying the cell type of a cell that has died from apoptosis. Cell type markers are those described above in the sixth aspect of the present invention.

Finally, the present invention also relates to apoptotic bodies isolable by the method of the invention according to the first aspect of the invention. A particular embodiment relates to an apoptotic body comprising CD90, GLAST, CD11b, CD100 or a tumour antigen in the outer membrane that can be isolated by the method of the invention. A more particular embodiment relates to an apoptotic body isolable by the method of the invention, comprising CD90, GLAST, CD11b o CD100 in the outer membrane.

All these advantages make the method of the isolation of apoptotic bodies described in the present invention an extremely valuable tool in daily clinical practice as a non-invasive method for determining the degree of cell death that has occurred in the patients, which would enable an earlier and more accurate prognosis, a more effective monitoring of the patient's evolution, and the selection of the most appropriate treatments for various pathologies, including neurodegenerative, vascular and oncological diseases. In this way, it provides a more personalised therapy that can alert a poor prognosis despite the fact that other clinical parameters may be favourable. At the same time, as already mentioned above, it is a method that can be performed from different body fluids, making it a method of quick and easy application, being also a method of easy interpretation, easily reproducible and of low economic cost.

EXAMPLES

The following are specific examples of the embodiment of the invention which serve to illustrate the invention without limiting the scope thereof.

Example 1

Isolation of Apoptotic Bodies. Purity

The trial includes 6 patients, two diagnosed with ischemic stroke (Patient 1: 85-year-old woman, Patient 2: 59-year-old man), two diagnosed with multiple sclerosis (Patient 3: 51-year-old woman, Patient 4: 32-year-old man), and two of Parkinson's disease (Patient 5: 61-year-old man, Patient 6: 68-year-old woman).

Blood (20 ml) from each patient was collected in the neurology service and deposited in tubes with sodium citrate. After less than 2 hours from extraction, the isolation of the apoptotic bodies was performed by means of serial centrifugations by the method of the first aspect of the invention, as indicated below:

Blood samples were subjected to centrifugation: 250 g for 10 min at 18° C. The plasma phase of the sample from patient 1 was diluted in a 1×TBS buffer in a ratio of 1:3 (step a1) and centrifuged at 850 g for 20 min at 18° C. (step b). The supernatant from the previous centrifugation was transferred to a clean polycarbonate tube and centrifuged at 12,000 g for 20 min at 9° C. (step c). The supernatant from the last centrifugation was eliminated and the sediment containing the apoptotic bodies was resuspended by pipetting in 1×TBS buffer.

Subsequently, the AB preparations were analysed by flow cytometry to determine the total number of microvesicles (MV) (Annexin V positive vesicles), including apoptotic bodies (AB), microparticles (MP) and exosomes (EXO) per milliliter of plasma. To this end, samples were incubated with Annexin-V and Propidium iodide (PI).

The results of this analysis are shown in table 1. Surprisingly, the total number of AB (positive for Annexin V and Propidium iodide for analysis by flow cytometry) isolated per milliliter of plasma represented more than 80% of the microvesicles obtained by the method of the invention, while the number of microparticles and exosomes (positive for annexin V and negative for Propidium iodide in analysis by flow cytometry) was less than 20% of the microvesicles. These findings demonstrate that the sediment and the AB preparations obtained by the process, object of the present invention, have a high degree of purity, that is, are minimally contaminated with other microvesicles.

TABLE 1

Purity of the sediment comprising the AB.

| | No. MV/ml plasma (Annexin V$^+$) | No. AB/ml plasma (Annexin V$^+$/IP$^+$) | No. MP + EXO/ml plasma (Annexin V$^+$/IP$^-$) |
|---|---|---|---|
| Patient 1 | 142,530 | 124,000 (87%) | 18,530 |
| Patient 2 | 93,902 | 77,000 (82%) | 16,902 |
| Patient 3 | 35,164 | 32,000 (91%) | 3,764 |
| Patient 4 | 44,705 | 38,000 (85%) | 6,705 |
| Patient 5 | 40,588 | 34,500 (85%) | 6,088 |
| Patient 6 | 44,681 | 42,000 (94%) | 2,681 |

Example 2

Isolation of Apoptotic Bodies. Performance

The trial includes 2 patients, two diagnosed with ischemic stroke (patient 1: 76-year-old man, Patient 2: 58-year-old man).

Blood (20 ml) from each patient was collected in the neurology service and deposited in tubes with sodium citrate. Within less than 2 hours after extraction, the isolation of apoptotic bodies was performed as follows:

Blood samples were subjected to centrifugation: 160 g for 20 min at 18° C. The plasma phase (containing the apoptotic bodies) of sample from patient 2 was transferred to a sterile polypropylene tube (step a) and centrifuged at 700 g for 30 min at 18° C. (step b). The plasma phase of the sample from patient 1 was diluted in a 1×TBS buffer in a ratio of 1:3 (step a1) and centrifuged at 700 g for 30 min at 18° C. (step b). The supernatant from the previous centrifugation was transferred to a clean polycarbonate tube and centrifuged at 14,000 g for 30 min at 9° C. (step c). The supernatant from the last centrifugation was eliminated and the sediment containing the apoptotic bodies was resuspended by pipetting in 1×TBS buffer.

In both cases, before proceeding to the isolation of apoptotic bodies, one part (1 ml) of plasma phase was removed to determine the number of apoptotic bodies per milliliter by flow cytometry (incubation with Annexin-V and Propidium iodide).

The preparations of intact apoptotic bodies with a high degree of purity (minimally contaminated with other microvesicles) obtained by the aforementioned protocol were also analysed by flow cytometry to determine the total number of apoptotic bodies per milliliter of plasma. To this end, the apoptotic bodies were incubated with Annexin-V and Propidium iodide.

The results of this analysis are shown in table 2. The total number of isolated apoptotic bodies per milliliter of plasma, represented 90% of apoptotic bodies present in plasma if they were obtained by the method of the invention including the step a1 (dilution), whereas the total number of apoptotic bodies accounted for 78% of the total present in plasma if this step was not included.

TABLE 2

Performance of the isolation

| | TOTAL No. AB/ml plasma | No. AB/ml plasma (isolation without dilution) | No. AB/ml plasma (isolation with dilution) |
|---|---|---|---|
| Patient 1 | 94,445 | 85,000 | — |
| Patient 2 | 173,075 | — | 135,000 |

Example 3

Ischemic Stroke

The trial includes two patients, a 78-year-old woman and a 70 year-old woman, who were attended by the Neurology service on suspicion of ischemic stroke. A simple CAT scan was performed under perfusion protocol, which showed ischemic injury in the area of the right middle cerebral artery in patient 1, and in the area of the left middle cerebral artery in patient 2. Below, are the reported clinical data for each patient;

aetiology as per TOAST classification:
Patient 1: Cerebral infarction of undetermined origin.
Patient 2: Cerebral infarction of cardioembolic origin.
radiological assessment: (i) initial (determination of the volume of initial infarction obtained from the CAT—perfusion test) and (ii) final, at 96 h from the onset of symptoms (a simple CAT scan was performed to determine final infarction volume).
Patient 1: initial infarction volume: 22,310 mm$^3$, infarction volume at 96 h: 57,127 mm$^3$. Ischemic lesion increased 2.5 folds during the first 96 h.
Patient 2: initial infarction volume: 5,080 mm$^3$, infarction volume at 96 h: 5,500 mm$^3$. There was an increase of the infarcted region during the first 96 h.
functional status according to the NIHSS scale: (i) initial and (ii) final, at 96 h post-stroke, which allows to determine the evolution of the cerebral infarction:
Patient 1: Progressive infarction (increase by more than 4 points on the scale).
Patient 2: Regressive infarction (decrease by more than 4 points on the scale).

Blood (20 ml) from each patient was collected and deposited in tubes with sodium citrate during the initial course and later at 96 h from the onset of the stroke symptoms. Within less than 2 hours after extraction, the isolation of apoptotic bodies was performed as follows:

Blood samples were subjected to centrifugation: 250 g for 10 min at 18° C. The plasma phase was transferred to a polypropylene sterile tube and diluted in a 1×TBS buffer in a ratio of 1:3 and centrifuged at 850 g for 20 min at 18° C. The supernatant from the previous centrifugation was transferred to a clean polycarbonate tube and centrifuged at 12,000 g for 20 min at 9° C. The supernatant from the last centrifugation was eliminated and the sediment containing the apoptotic bodies was resuspended by pipetting in 1×TBS buffer.

Subsequently, preparations of whole AB with a high degree of purity were analysed by flow cytometry to determine the total number of AB per milliliter of plasma coming from the death of cells of the nervous system (microglia, oligodendrocytes, astrocytes and neurons) from each patient. To this end, the apoptotic bodies were incubated with Annexin-V, propidium iodide and antibodies, anti-CD11b, anti-CD100, anti-CD90 and anti-GLAST.

The results of this analysis are shown in FIG. 1. In patient 1, with a progressive infarction and who experienced an increase of ischemic injury within 96 hours from the onset of stroke symptoms, a significant increase in the AB levels was detected derived from the death of nervous tissue, while in patient 2, with a regressive infarction and without increase of the ischemic region, the AB concentration decreased significantly after 96 hours post-infarction.

Therefore, these results indicate that the quantification of apoptotic bodies of glial and neuronal origin isolated by the object procedure of the present invention is a marker of brain death that allows effective monitoring of cerebral ischemia, as well as the precise determination of prognosis or course of the infarcted patient. This information would greatly help the development and selection of appropriate treatments for each patient (personalised therapy).

Example 4

Ischemic Stroke

The trial includes two patients, a 76-year-old man and an 85 year-old man, who were attended by the Neurology service suspected of an ischemic stroke. Initial radiological assessment showed that patient 1 had no brain ischemic lesions, and patient 2 had a volume of cerebral infarction of 17,455 mm$^3$. The complete neurologic examination determined that patient 1 suffered a TIA with full functional recovery, while patient 2 had an ischemic stroke of atherothrombotic origin.

Blood (20 ml) from each patient was collected and deposited in tubes with sodium citrate during the initial course. Within less than 2 hours after extraction, the isolation of apoptotic bodies was performed as follows:

Blood samples were subjected to centrifugation: 160 g for 20 min at 18° C. The plasma phase was transferred to a polypropylene sterile tube and centrifuged at 700 g for 30 min at 18° C. The supernatant from the previous centrifugation was transferred to a clean polycarbonate tube and centrifuged at 14,000 g for 30 min at 9° C. The supernatant from the last centrifugation was eliminated and the sediment containing the apoptotic bodies was resuspended by pipetting in a 1×PBS buffer.

Subsequently, the preparations of the intact apoptotic bodies with a high degree of purity were analysed by flow cytometry to determine the total number of AB per milliliter of plasma. To this end, the apoptotic bodies were incubated with Annexin-V and Propidium iodide.

The results of this analysis are shown in FIG. 2. Quantification of AB revealed that patient 1, who did not suffer an ischemic stroke but a TIA, initially had plasma levels eleven times lower than those detected in patient 2, with an established ischemic stroke. These findings demonstrate that the quantification of AB isolated by the procedure, object of the present invention, has clinical utility in the establishment of an early and accurate diagnosis of cerebrovascular disease.

Example 5

Ischemic Stroke

The trial includes two patients, a 45-year-old man and a 58 year-old man, who were attended by the Neurology service on suspicion of ischemic stroke. The early radiological evaluation showed that patient 1 had no cerebral ischemic lesions, and patient 2 had a volume of cerebral infarction of 12,300 mm$^3$. The complete neurologic examination determined that patient 1 suffered a TIA with full functional recovery, while patient 2 had an ischemic stroke of atherothrombotic origin.

Blood (20 ml) was collected from each patient and deposited in tubes with sodium citrate during initial course. Within less than 2 hours after extraction, the isolation of apoptotic bodies was performed by serial centrifugations. Below is detailed the extraction protocol of apoptotic bodies, which is the object of the present invention:

Blood samples were subjected to centrifugation: 160 g for 20 min at 18° C. The plasma phase was transferred to a polypropylene sterile tube and was diluted in a 1×PBS buffer in a ratio of 1:3 and centrifuged at 700 g for 30 min at 18° C. The supernatant from the previous centrifugation was transferred to a clean polycarbonate tube and centrifuged at 14,000 g for 30 min at 9° C. The supernatant from the last centrifugation was eliminated and the sediment containing the apoptotic bodies was resuspended by pipetting in 1×PBS buffer.

Subsequently, the preparations of intact apoptotic bodies with a high purity degree were analysed by flow cytometry to determine the total number of apoptotic bodies per milliliter of plasma. To this end, the apoptotic bodies were incubated with Annexin-V and Propidium iodide.

The results of this analysis are shown in FIG. 3. Quantification of apoptotic bodies revealed that patient 1, who had not suffered an ischemic stroke but a TIA, had initially plasma levels fifteen times lower than those detected in patient 2, with an established ischemic stroke. These findings demonstrate that the quantification of apoptotic bodies isolated by the procedure, object of the present invention, has clinical utility for the establishment of an early and accurate diagnosis of the cerebrovascular disease.

Example 6

Multiple Sclerosis

The trial included two patients, a 38-year-old man and a 44-year-old woman diagnosed with Relapsing-Remitting Multiple Sclerosis (RRMS) with 2 and 3 years of development and a score on the EDSS scale (Expanded Disability Status Scale) of 1 and 0 respectively. Patient 1 received treatment with Interferon Beta and patient 2 with Natalizumab.

Blood (20 ml) from each patient (in situation of absence of outbreak, clinically stable) was collected and deposited in tubes with sodium citrate. Within less than 2 hours after extraction, the isolation of AB was performed as follows:

Blood samples were subjected to centrifugation: 200 g for 15 min at 18° C. The plasma phase was transferred to a polypropylene sterile tube and was diluted in a 10 mM Hepes buffer in a ratio of 1:3 and centrifuged at 600 g for 40 min at 18° C. The supernatant from the previous centrifugation was transferred to a clean polycarbonate tube and centrifuged at 13,000 g for 30 min at 9° C. The supernatant from the last centrifugation was eliminated and the sediment containing the apoptotic bodies was resuspended by pipetting in a 10 mM Hepes buffer.

Subsequently, the preparations of intact AB with a high degree of purity were analysed by flow cytometry as indicated in example 3.

The results of this analysis are shown in FIG. 4. In patient 1, under Beta Interferon therapy, the number of plasma AB proceeding from the death of neurons, astrocytes and oligodendrocytes was approximately two times higher than detected in patient 2, who was being was treated with Natalizumab.

Therefore, these results indicate that the quantification of AB of neuronal and glial origin isolated by the procedure, object of the present invention, allows evaluating the efficacy of drugs in multiple sclerosis disease, facilitating the selection of the most appropriate treatments for each patient (personalised therapy).

Example 7

Multiple Sclerosis

The trial included 4 patients diagnosed with multiple sclerosis, 1 man and 3 women with an average age of 30.5 years (range 21-41). Patient 1 and 2 were in the early stage or phase, whereas patients 3 and 4 were in the advanced stage of the disease.

Blood (20 ml) from each patient was collected in the neurology service and deposited in tubes with sodium citrate. After less than 2 hours from extraction, the isolation of AB was performed by serial centrifugation, as indicated in the previous example.

Subsequently, the preparations of intact AB with a high degree of purity were analysed by flow cytometry to determine the total number of apoptotic bodies per milliliter of plasma. To this end, the apoptotic bodies were incubated with Annexin-V and Propidium iodide.

Figure 5:
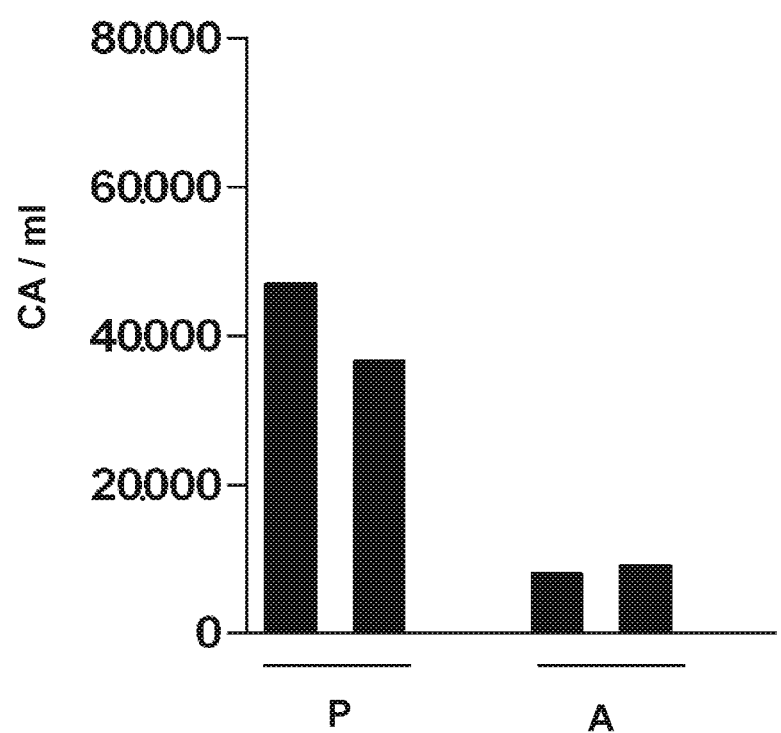
FIG. 5: Graphic representation of the number of AB per milliliter of plasma in four patients diagnosed with relapsing-remitting multiple sclerosis, two patients in an early stage (P) and two patients in an advanced stage (A).

The results of this analysis are shown in FIG. 5. As shown in FIG. 5, the plasma concentration of apoptotic bodies in patients undergoing the early stage or phase (41,765±7,300 AB/ml plasma) is clearly higher than detected in patients in a more advanced stage (8,585±726 AB/ml plasma). These results support the clinical value of the plasma concentration of the AB isolated by the procedure, object of the present invention (non-invasive method for the isolation of intact apoptotic bodies and bodies minimally contaminated with other microvesicles), in the early detection and staging of Multiple Sclerosis.

Example 8

Parkinson's Disease

The trial included 6 patients diagnosed with Parkinson's disease, 4 men and 2 women, with an average age of 68 years (range 49-81). The cohort of study subjects was homogeneously distributed in the three first stages of the pathology (I, n=2; II, n=2, and III, n=2).

Blood (20 ml) from each patient was collected in the neurology service and deposited in tubes with sodium citrate. Within less than 2 hours after extraction, the isolation of AB was performed by the method described in example 3.

Subsequently, the preparations of intact AB with a high degree of purity (minimally contaminated with other microvesicles) were analysed by flow cytometry to determine the total number of AB per milliliter of plasma. To this end, the AB were incubated with Annexin-V and Propidium iodide.

Figure 6:
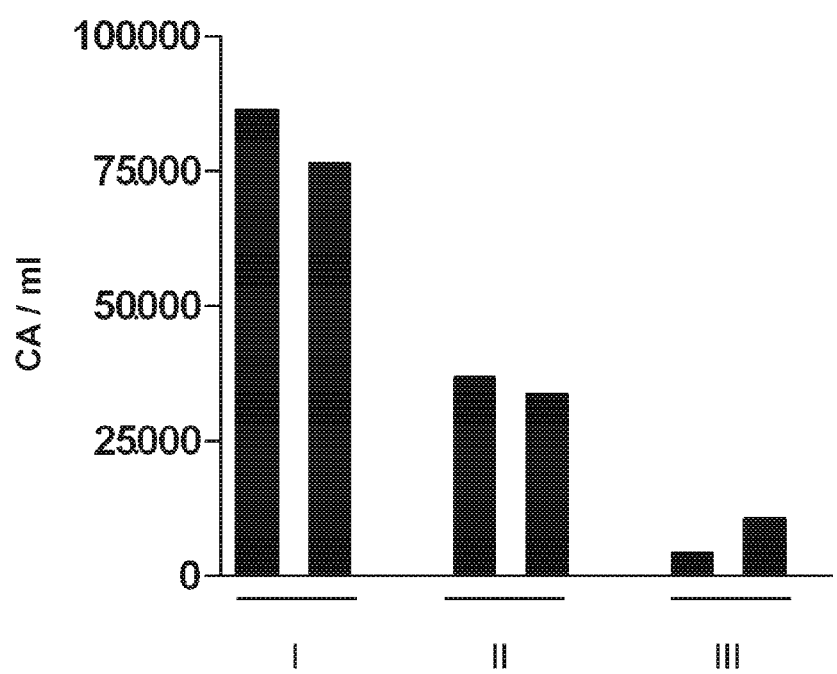
FIG. 6: Graphic representation of the number of AB per milliliter of plasma in six patients diagnosed with Parkinson's disease, two patients in each of the early stages of the disease (I, II and III).

The results of this analysis are shown in FIG. 6. As shown in the figure, the plasma concentration of AB from patients undergoing the stage I (81,513±7,000 AB/ml plasma) is clearly higher than detected in patients in stage II (35,277±2,255 AB/ml plasma) and in stage III (7,565±3,000 AB/ml plasma). These results support the clinical value of the plasma concentration of the AB isolated by the procedure, object of the present invention, in the early detection and staging of Parkinson's disease.

Example 9

Metastatic Colon Cancer

The trial included 3 patients diagnosed with metastatic colon cancer (metastases located in the liver) and treated at the general surgery service. Patient 1, a 70 year-old woman, and patient 2, a 72-year-old man, had received 6 cycles of chemotherapy treatment with FOLFIRI (Irinotecan, 5-Fluorouracil and polinic acid), while patient 3, a 71-year-old woman, did not receive chemotherapy.

Blood (20 ml) from each patient was collected after finishing the anti-tumour treatment and deposited in tubes with sodium citrate. Within less than 2 hours after extraction, the isolation of AB was performed by the method described in example 5.

Subsequently, the preparations of intact AB with a high degree of purity were analysed by flow cytometry to determine the total number of AB per milliliter of plasma. To this end, the AB were incubated with Annexin-V and Propidium iodide.

Figure 7:
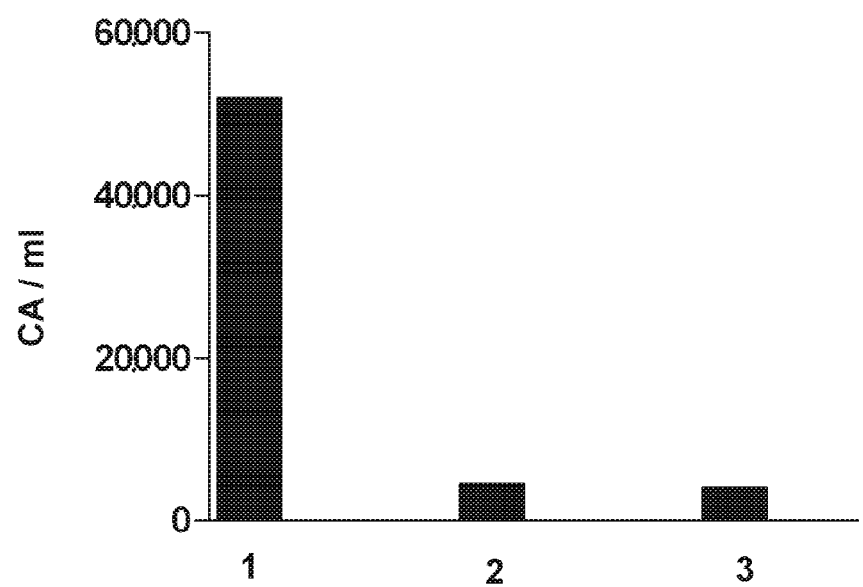
FIG. 7: Graphic representation of the number of AB per milliliter of plasma in three patients (1, 2 and 3) diagnosed with metastatic colon cancer. Patient 1 and patient 2 had received 6 cycles of chemotherapy treatment with FOLFIRI while patient 3 did not receive any chemotherapy.

The results of this analysis are shown in FIG. 7. Quantification of AB revealed that patient 1, once the antineoplastic therapy had finished, had a plasma concentration of AB 10 times higher than detected in patient 2, after treatment, and higher than that the found in patient 3, who had not received chemotherapy. Interestingly, the radiological examinations on the patients showed that only patient 1 had experienced a reduction in tumour size of the liver metastases, indicating a good response to the anti-tumour treatment. These data demonstrate that the determination of plasma levels of AB isolated by the procedure, object of the present invention, allows the assessment of the response to chemotherapy in patients with metastatic colon cancer.

The invention claimed is:

1. A method for isolating apoptotic bodies from a sample of body fluid comprising:
    A) centrifuging a sample of body fluid taken from a subject, at a speed of 300 g or less, and collecting the supernatant,
    B) centrifuging the supernatant obtained in step A) at a speed between 400 g and 1,000 g and collecting the supernatant, and
    C) centrifuging the supernatant obtained in step B) at a speed between 8,000 g and 40,000g and eliminating the supernatant,
    wherein centrifuging the sample in step A) and the supernatant in steps B), and C) is carried out at a temperature between 8° C. and 25° C. for at least 5 minutes, and the sediment obtained in step C) comprises the isolated apoptotic bodies, wherein the apoptotic bodies are membrane vesicles of a size from 1 μm to 4 μm, caused by cell fragmentation of dead cells from apoptosis, and which comprise nuclear fragments, genetic material and cytoplasmic constituents of apoptotic cells, and wherein the apoptotic bodies are positive for propidium iodide staining in a flow cytometry analysis.

2. The method according to claim 1, wherein the body fluid is selected from the group consisting of blood, plasma, urine, cerebrospinal fluid, ascetic fluid, synovial fluid and amniotic fluid.

3. The method according to claim 1, wherein the body fluid is blood.

4. The method according to claim 1, wherein centrifuging the supernatant in step B) is at a speed between 500 g to 800 g.

5. The method according to claim 1, wherein centrifuging in step C) is at a speed between 11,000 g to 30,000 g.

6. The method according to claim 1, wherein between steps A) and B) a step A1) is carried out, in which the supernatant obtained in step A) is diluted in a buffer.

7. The method according to claim 1, wherein centrifuging the supernatant in step B) is at a speed between 500 g to 800 g and centrifuging the supernatant in step C) is at a speed between 11,000 g to 30,000 g.

8. The method according to claim 6, wherein centrifuging the supernatant in step B) is at a speed between 500 g to 800 g and centrifuging the supernatant in step C) is at a speed between 11,000 g to 30,000 g.

\* \* \* \* \*